US010155990B2

(12) United States Patent
Abe et al.

(10) Patent No.: US 10,155,990 B2
(45) Date of Patent: *Dec. 18, 2018

(54) METHOD FOR PREDICTING THERAPEUTIC EFFICACY OF PI3K/AKT/MTOR INHIBITOR ON BASIS OF PHLDA1 OR PIK3C2B EXPRESSION (71) Applicant: Taiho Pharmaceutical Co., Ltd., Chiyoda-ku, Tokyo (JP)

(72) Inventors: Tetsuya Abe, Tsukuba (JP); Hiraku Itakdani, Tsukuba (JP)

(73) Assignee: Taiho Pharmaceuticals, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/895,286

(22) PCT Filed: Jun. 19, 2014

(86) PCT No.: PCT/JP2014/066255
§ 371 (c)(1),
(2) Date: Dec. 2, 2015

(87) PCT Pub. No.: WO2014/203959
PCT Pub. Date: Dec. 24, 2014

(65) Prior Publication Data
US 2016/0102366 A1 Apr. 14, 2016

(30) Foreign Application Priority Data

Jun. 20, 2013 (JP) ................. 2013-129591

(51) Int. Cl.
A61K 31/366 (2006.01)
C12Q 1/6886 (2018.01)
A61K 31/5365 (2006.01)
G01N 33/574 (2006.01)
A61K 31/436 (2006.01)
A61K 31/4155 (2006.01)
A61K 31/519 (2006.01)
A61K 31/52 (2006.01)
A61K 31/5377 (2006.01)
A61K 31/7064 (2006.01)
A61K 31/4375 (2006.01)
A61K 31/4745 (2006.01)

(52) U.S. Cl.
CPC .......... *C12Q 1/6886* (2013.01); *A61K 31/366* (2013.01); *A61K 31/4155* (2013.01); *A61K 31/436* (2013.01); *A61K 31/4375* (2013.01); *A61K 31/4745* (2013.01); *A61K 31/519* (2013.01); *A61K 31/52* (2013.01); *A61K 31/5365* (2013.01); *A61K 31/5377* (2013.01); *A61K 31/7064* (2013.01); *G01N 33/57484* (2013.01); *G01N 33/57496* (2013.01); *C12Q 2600/106* (2013.01); *C12Q 2600/118* (2013.01); *C12Q 2600/158* (2013.01); *G01N 2333/4703* (2013.01); *G01N 2333/91215* (2013.01); *G01N 2800/52* (2013.01)

(58) Field of Classification Search
CPC ..................................................... A61K 31/366
USPC ..................................................... 514/234.2
See application file for complete search history.

(56) References Cited

U.S. PATENT DOCUMENTS

| 8,772,283 | B2 * | 7/2014 | Nakamura | ........... | C07D 498/04 |
| | | | | | 514/230.2 |
| 9,375,434 | B2 * | 6/2016 | Ichikawa | ............. | A61K 31/337 |
| 2009/0023149 | A1 * | 1/2009 | Knudsen | ............. | C12Q 1/6886 |
| | | | | | 435/6.14 |
| 2014/0005185 | A1 | 1/2014 | Nakamura et al. | | |

FOREIGN PATENT DOCUMENTS

| EP | 2802586 | | 11/2014 | | |
| WO | WO 2010/087497 | * | 5/2010 | ............. | A61K 38/00 |
| WO | 2010/087497 A1 | | 8/2010 | | |
| WO | 2012/137870 A1 | | 10/2012 | | |
| WO | 2013104610 A1 | | 7/2013 | | |

OTHER PUBLICATIONS

Liu et al. Phosatidylinositol 3-kinase pathway in cancer, Nature Reviews Drug Discovery, 2009, 8(8), 627-644.*
Liu et al., Nature Reviews Drug Discovery, 2009,8(8), 627-644.*
Wang. et al . Proceedings of the 103rd Annual Meeting of the AACR Chicago, Cancer Research, 72(8), 2012.*
Traer et al. Electronic Journal of Oncology, Bull Cancer, 2006, vol. 93 , No. 5 ,E53-58. , Bull Cancer, 2006, vol. 93 , No. 5 ,E53-58.*
Liu et al. The Journal of International Medical Research ,2011, 39(4), 1319-1332.*
Garrido-Laguna et al. British Journal of Cancer (2010) 103, 649-655.*
Venkatesh et al., J. Pharm. Sci. 89, 145-54 (2000).*
Dienstmann Mol Cancer Ther; 13(5); 1021-31. 2014.*
Freshney (Culture of Animal Cells, A Manual of Basic Technique, Alan R. Liss, Inc., 1983, New York, p. 4).*
Arcaro et al., "Two distinct phosphoinositide 3-kinases mediate polypeptide growth factor-stimulated PKB activation", The EMBO Journal, 2002, vol. 21, No. 19, pp. 5097-5108.
De Roock et al., "KRAS, BRAF, PIK3CA, and PTEN mutations: implications for targeted therapies in metastatic colorectal cancer", Lancet Oncology, 2011, vol. 12, pp. 594-603.

(Continued)

Primary Examiner — Nizal S Chandrakumar
(74) Attorney, Agent, or Firm — Rothwell, Figg, Ernst & Manbeck, P.C.

(57) ABSTRACT

An object of the present invention is to provide a chemotherapy using a PI3K/AKT/mTOR inhibitor that produces an excellent antitumor effect on a cancer patient. The present invention provides a method for predicting the therapeutic efficacy of the chemotherapy using the antitumor agent comprising a PI3K/AKT/mTOR inhibitor on a cancer patient on the basis of the expression level of PHLDA1 and/or PIK3C2B in a biological sample containing tumor cells isolated from the cancer patient.

7 Claims, 2 Drawing Sheets (56) References Cited

OTHER PUBLICATIONS

Domin et al., "The Class II Phosphoinositide 3-Kinase PI3K-C2β Regulates Cell Migration by a PtdIns(3) P Dependent Mechanism", Journal of Cellular Physiology, 2005, vol. 205, No. 3, pp. 452-462.
Engelman, "Targeting PI3K signalling in cancer; opportunities, challenges and limitations", Nature Reviews Cancer, 2009, vol. 9, pp. 550-562.
La et al., "Predictive biomarkers: a paradigm shift towards personalized cancer medicine", Nature Reviews Clinical Oncology, 2011, vol. 8, pp. 587-596.
Liu et al, "Targeting the phosphoinositide 3-kinase pathway in cancer", Nature Reviews Drug Discovery, 2009, vol. 8, No. 8, pp. 627-644.
Liu et al., "Phosphatidylinositol 3-kinase-C2β Inhibits Cisplatin-mediated Apoptosis via the Akt Pathway in Oesophageal Squamous Cell Carcinoma", The Journal of International Medical Research, 2011, vol. 39, No. 4, pp. 1319-1332.
Traer et al., "Are class II phosphoinositide 3-kinases potential targets for anticancer therapies?", Bulletin du Cancer, 2006, vol. 93, No. 5, pp. 53-58.
Vivanco et al., "The phosphatidylinositol 3-Kinase-AKT pathway in human cancer", Nature Reviews Cancer, 2002, vol. 2, pp. 489-501.
Wang et al., "Abstract 20: PHLDA1/2 contribute to tumor suppression in breast and lung cancer as downstream targets of oncogenic HER2 signalling", Cancer Research, 2012, vol. 72, Issue 8, Supplement 1.
Yunokawa et al., "Efficacy of everolimus, a novel mTOR inhibitor, against basal-like triple-negative breast cancer cells", Cancer Sci, Sep. 2012, vol. 103, No. 9, pp. 1665-1671.
Shi et al., "Enhanced Sensitivity of Multiple Myeloma Cells Containing PTEN Mutations to CCI-779", Cancer Research, 62, Sep. 1, 2002, pp. 5027-5034.
Boller et al., "Targeting PI3KC2β Impairs Proliferation and Survival in Acute Leukemia, Brain Tumours and Neuroendocrine Tumours", Anti Cancer Research, Jan. 2012, pp. 3015-3028.
Knobbe et al., "Genetic Alterations and Aberrant Expression of Genes Related to the Phosphatidyl-Inositol-3'-Kinase/Protein Kinase B (Akt) Signal Transduction Pathway in Glioblastomas", Brain Pathology, vol. 13, No. 4, 2003, pp. 507-518.
Dan et al., "Correlating Phosphatidylinositol 3-Kinase Inhibitor Efficacy with Signaling Pathway Status: In silico and Biological Evaluations", Cancer Research, vol. 70, No. 12, 2010, pp. 4982-4994.
Sadeghi et al., "Targeting the PI3K pathway for cancer therapy", Future Medicinal Chemistry, vol. 4, No. 9, Jun. 2012, pp. 1153-1169.
Extended European Search Report for Application No. 14813575. 9-1466 dated Feb. 22, 2017, 15 pages.
Kwei et al., "Modulators of Sensitivity and Resistance to Inhibition of PI3K Identified in a Pharmacogenomic Screen of the NCI-60 Human Tumor Cell Line Collection", PLOS One, 2012, vol. 7, No. 9, e46518, 13 pages.
Noh et al., "Determinants of Rapamycin Sensitivity in Breast Cancer Cells", Clinical Cancer Research, 2004, vol. 10, pp. 1013-1023.
O'Reilly and McSheehy, "Biomarker Development for the Clinical Activity of the mTOR Inhibitor Everolimus (RAD001): Processes, Limitations, and Further Proposals", Translational Oncology, 2010, vol. 3, No. 2 pp. 65-79.
Examination Report No. 2 for the corresponding AU patent application No. 2014282179, dated May 15, 2017, 6 pages.
Wen et al., "Current clinical development of PI3K pathway inhibitors in glioblastoma", Neuro-Oncology, 14(7): 819-829, 2012.
Office Action for Russian Patent Application No. 2016101364 dated Jan. 11, 2018, 8 pages with translation.
Anderson, "Practical Process Research & Development, Chapter 11, Tools for Purifying the Product: Column Chromatography, Crystallization and Reslurrying", 2000, Practical Process Research & Development, pp. 223-224.
Byrn et al., "Pharmaceutical Solids: A strategic Approach to Regulatory Considerations", Pharmaceutical Research, vol. 12, No. 7, 1995, pp. 945-954.
Extended European Search Report cited in European Application No. 16755672.9 dated Jul. 13, 2018, 7 pages.

\* cited by examiner

METHOD FOR PREDICTING THERAPEUTIC EFFICACY OF PI3K/AKT/MTOR INHIBITOR ON BASIS OF PHLDA1 OR PIK3C2B EXPRESSION

CROSS REFERENCE TO RELATED APPLICATION

This application is a 35 U.S.C. 371 National Phase Entry Application from PCT/JP2014/066255, filed Jun. 19, 2014, which claims the benefit of Japanese Patent Application No. 2013-129591 filed on Jun. 20, 2013, the disclosure of which is incorporated by reference in its entirety.

TECHNICAL FIELD

The present invention relates to a method for predicting the therapeutic efficacy of a chemotherapy using an antitumor agent comprising a PI3K/AKT/mTOR inhibitor, an antitumor agent, and a kit.

BACKGROUND ART

The PI3K/AKT/mTOR signaling pathway regulates various important cell functions such as cell proliferation, apoptosis resistance, and glycometabolism. The pathway is known to be hyperactive in a broad range of malignant tumors (Non-Patent Literature 1). Clinical trials have been conducted on many PI3K/AKT/mTOR inhibitors used as an antitumor agent (e.g., PI3K inhibitor, AKT inhibitor, mTOR inhibitor, or PI3K-mTOR dual inhibitor). However, particularly in clinical trials using a PI3K or AKT-targeting inhibitor as a single drug, none of these have yet to demonstrate satisfactory clinical benefits (Non-Patent Literature 2).

Molecularly targeted drugs, such as PI3K/AKT/mTOR inhibitors, may typically exhibit high potency on tumor cells in which the target molecules are highly expressed or hyperactive. It is thus important to stratify patients by using a therapeutic efficacy predictive marker to select a group of patients for whom beneficial effects are expected (Non-Patent Literature 3). As for PI3K/AKT/mTOR inhibitors, PIK3CA mutation, PTEN deletion, and the like have been examined as a therapeutic efficacy predictive marker in clinical practice (Non-Patent Literature 4).

As noted above, a variety of PI3K/AKT/mTOR inhibitors have been intensively developed. Nonetheless, their therapeutic efficacy on all cancer patients has remained unsatisfactory, and there has been found no therapeutic efficacy predictive markers capable of stratifying patients to select a group of patients that are likely to sufficiently respond to the PI3K/AKT/mTOR inhibitors.

CITATION LIST

Non-Patent Literature

Non-Patent Literature 1: Nature Reviews Cancer 2, 489-501 (2002)
Non-Patent Literature 2: Nature Reviews Cancer 9, 550-562 (2009)
Non-Patent Literature 3: Nature Reviews Clinical Oncology 8, 587-596 (2011)
Non-Patent Literature 4: Lancet Oncology 12, 594-603 (2011)

SUMMARY OF INVENTION

Technical Problem

An object of the present invention is to provide a chemotherapy using a PI3K/AKT/mTOR inhibitor that produces an excellent antitumor effect in a cancer patient.

Solution to Problem

The present inventors conducted extensive research on the relation between the expression of various genes and the therapeutic efficacy of PI3K/AKT/mTOR inhibitors, and found that PI3K/AKT/mTOR inhibitors (in particular, trans-3-amino-1-methyl-3-(4-(3-phenyl-5H-imidazo[1,2-c]pyrido[3,4-e][1,3]oxazin-2-yl)phenyl)cyclobutanol) have a significantly high antitumor effect on cancer patients exhibiting a low expression level of PHLDA1 or a high expression level of PIK3C2B. The inventors then completed the invention.

There have been no reports on the relation of PI3K/AKT/mTOR inhibitors to either PHLDA1 or PIK3C2B.

Specifically, the present invention provides the following method, antitumor agent, and kit.

Item 1.

A method for predicting therapeutic efficacy of a chemotherapy using an antitumor agent comprising a PI3K/AKT/mTOR inhibitor on a cancer patient on the basis of an expression level of PHLDA1 and/or PIK3C2B in tumor cells isolated from the cancer patient.

Item 2.

The method according to Item 1, comprising the following steps (1) and (2):

(1) measuring an expression level of PHLDA1 and/or PIK3C2B in a biological sample containing tumor cells isolated from the patient; and (2) predicting that the patient is likely to sufficiently respond to the chemotherapy using the antitumor agent comprising a PI3K/AKT/mTOR inhibitor when the expression level of PHLDA1 measured in step (1) is equal to or lower than a predetermined cutoff point, or when the expression level of PIK3C2B measured in step (1) is equal to or higher than a predetermined cutoff point.

Item 3.

The method according to Item 1 or 2, wherein the PI3K/AKT/mTOR inhibitor is an imidazo-oxazine compound represented by formula (I) or its pharmaceutically acceptable salt wherein A, B, C, and D represent C—$R^{1a}$, C—$R^{1b}$, C—$R^{1c}$, and C—$R^{1d}$, respectively, or one or two of the thus-defined A, B, C, and D are replaced by nitrogen;

at least two of $R^{1a}$, $R^{1b}$, $R^{1c}$, and $R^{1d}$ represent hydrogen, and the halogen, cyano, $C_{2-6}$ alkyl optionally substituted with one or more hydroxyl groups, $C_{1-6}$ alkoxy, carbonyl having hydroxyl, amino, optionally substituted mono- or di($C_{1-6}$ alkyl)amino or mono- or di($C_{1-6}$ alkoxy)amino as a substituent, or unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxyl;

or the PI3K/AKT/mTOR inhibitor is AMG-319, AZD-6482, BYL-719, copanlisib (BAY-80-6946), GDC-0032, GDC-0084, GSK-1059615, GSK-2126458, GSK-2636771, idelalisib (CAL-101), IPI-145, MLN-1117 (INK-1117), PA-799 (CH-5132799), pictilisib (GDC-0941), pilaralisib (XL-147), SF-1126, sonolisib (PX-866), voxtalisib (SAR-245409, XL-765), afuresertib hydrochloride (GSK-2110183), ARQ-092, AZD5363, enzastaurin hydrochloride, GDC-0068, GSK-2141795, GSK690693, LY-2780301, MK-2206, perifosine, triciribine phosphate (VQD-002), AZD-2014, AZD-8055, CC-115, CC-223, DS-3078, everolimus, temsirolimus, ME-344, MLN-0128 (INK-128), OSI-027, PWT-33597, ridaforolimus, sirolimus, dactolisib (BEZ235), DS-7423, GDC-0980, NVP-BGT-226, PF-04691502, PF-05212384 (PKI-587), or PWT-33597.

Item 4.

The method according to Item 3, wherein the imidazo-oxazine compound represented by formula (I) is a compound wherein A, B, C, and D represent C—$R^{1a}$, C—$R^{1b}$, C—$R^{1c}$, and C—$R^{1d}$, respectively, or any one or two of the thus-defined A, B, C, and D are replaced by nitrogen;

at least two of $R^{1a}$, $R^{1b}$, $R^{1c}$, and $R^{1d}$ represent hydrogen, and the other(s) each represent(s) chlorine, fluorine, cyano, methyl, hydroxymethyl, methoxy, ethoxy, carboxyl, carbamoyl, methylaminocarbonyl, ethylaminocarbonyl, hydroxyethylaminocarbonyl, ethoxyaminocarbonyl, or pyrazolyl;

$R^2$ represents phenyl, pyridyl, or thienyl;

$R^3$ represents hydrogen, methyl, ethyl, or cyclopropyl; and $R^4$ represents hydrogen or hydroxyl.

Item 5.

The method according to Item 3 or 4, wherein the imidazo-oxazine compound represented by formula (I) is any of the following compounds (a) to (t), (a) trans-3-amino-1-cyclopropyl-3-(4-(10-fluoro-3-phenyl-5H-benzo[e]imidazo[1,2-c][1,3]oxazin-2-yl)phenyl)cyclobutanol, (b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol, (c) trans-3-amino-1-cyclopropyl-3-(4-(3-phenyl-5H-benzo[e]imidazo[1,2-c][1,3]oxazin-2-yl)phenyl)cyclobutanol, (d) trans-3-amino-1-cyclopropyl-3-(4-(10-methoxy-3-phenyl-5H-benzo[e]imidazo[1,2-c][1,3]oxazin-2-yl)phenyl)cyclobutanol, (e) trans-3-amino-1-cyclopropyl-3-(4-(9-methoxy-3-phenyl-5H-benzo[e]imidazo[1,2-c][1,3]oxazin-2-yl)phenyl)cyclobutanol, (f) trans-3-amino-1-cyclopropyl-3-(4-(8-methoxy-3-phenyl-5H-benzo[e]imidazo[1,2-c][1,3]oxazin-2-yl)phenyl)cyclobutanol, (g) trans-3-amino-1-cyclopropyl-3-(4-(3-phenyl-5H-imidazo[1,2-c]pyrido[2,3-e][1,3]oxazin-2-yl)phenyl)cyclobutanol, (h) trans-3-amino-1-methyl-3-(4-(3-phenyl-5H-imidazo[1,2-c]pyrido[2,3-e][1,3]oxazin-2-yl)phenyl)cyclobutanol, (i) trans-3-amino-1-ethyl-3-(4-(3-phenyl-5H-imidazo[1,2-c]pyrido[2,3-e][1,3]oxazin-2-yl)phenyl)cyclobutanol, (j) trans-3-amino-1-cyclopropyl-3-(4-(3-phenyl-5H-imidazo[1,2-c]pyrido[3,4-e][1,3]oxazin-2-yl)phenyl)cyclobutanol, (k) trans-3-amino-1-methyl-3-(4-(3-phenyl-5H-imidazo[1,2-c]pyrido[3,4-e][1,3]oxazin-2-yl)phenyl)cyclobutanol, (l) trans-3-amino-1-cyclopropyl-3-(4-(3-phenyl-5H-imidazo[1,2-c]pyrido[4,3-e][1,3]oxazin-2-yl)phenyl)cyclobutanol, (m) trans-3-amino-1-methyl-3-(4-(3-phenyl-5H-imidazo[1,2-c]pyrido[4,3-e][1,3]oxazin-2-yl)phenyl)cyclobutanol, (n) trans-3-amino-1-cyclopropyl-3-(4-(3-phenyl-5H-imidazo[1,2-c]pyrido[3,2-e][1,3]oxazin-2-yl)phenyl)cyclobutanol, (o) trans-3-amino-1-cyclopropyl-3-(4-(3-phenyl-5H-imidazo[1,2-c]pyrazino[2,3-e][1,3]oxazin-2-yl)phenyl)cyclobutanol, (p) trans-3-amino-3-(4-(9-(hydroxymethyl)-3-phenyl-5H-benzo[e]imidazo[1,2-c][1,3]oxazin-2-yl)phenyl)-1-methylcyclobutanol, (q) 2-(4-(trans-1-amino-3-hydroxy-3-methylcyclobutyl)phenyl)-3-phenyl-5H-benzo[e]imidazo[1,2-c][1,3]oxazine-9-carbonitrile, (r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol, (s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and (t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

Item 6.

The method according to any one of Items 1 to 5, wherein the PI3K/AKT/mTOR inhibitor is MK-2206, BEZ235, GDC-0941, sirolimus, or trans-3-amino-1-methyl-3-(4-(3-phenyl-5H-imidazo[1,2-c]pyrido[3,4-e][1,3]oxazin-2-yl)phenyl)cyclobutanol.

Item 7.

An antitumor agent for treating a cancer patient, the antitumor agent comprising a PI3K/AKT/mTOR inhibitor, and the cancer patient having tumor cells in which an expression level of PHLDA1 is equal to or lower than a predetermined cutoff point or an expression level of PIK3C2B is equal to or higher than a predetermined cutoff point.

Item 8.

An antitumor agent comprising a PI3K/AKT/mTOR inhibitor, the antitumor agent being administered to a patient who is predicted to be likely to sufficiently respond to a chemotherapy using the antitumor agent by a method comprising the following steps (1) and (2):

(1) measuring an expression level of PHLDA1 and/or PIK3C2B in a biological sample containing tumor cells isolated from the patient; and (2) predicting that the patient is likely to sufficiently respond to the chemotherapy using the antitumor agent comprising a PI3K/AKT/mTOR inhibitor when the expression level of PHLDA1 measured in step (1) is equal to or lower than a predetermined cutoff point, or when the expression level of PIK3C2B measured in step (1) is equal to or higher than a predetermined cutoff point.

Item 9.

A kit comprising a reagent for measuring an expression level of PHLDA1 and/or PIK3C2B, the kit being for predicting therapeutic efficacy of a chemotherapy using an antitumor agent comprising a PI3K/AKT/mTOR inhibitor on a cancer patient by a method comprising the following steps (1) and (2):

(1) measuring an expression level of PHLDA1 and/or PIK3C2B in a biological sample containing tumor cells isolated from the patient; and (2) predicting that the patient is likely to sufficiently respond to the chemotherapy using the antitumor agent comprising a PI3K/AKT/mTOR inhibitor when the expression level of PHLDA1 measured in step (1) is equal to or lower than a predetermined cutoff point, or when the expression level of PIK3C2B measured in step (1) is equal to or higher than a predetermined cutoff point.

Item 10.

A method for treating a cancer patient, the method comprising administering an antitumor agent comprising a PI3K/AKT/mTOR inhibitor to a patient who is predicted by the method according to any one of Items 1 to 6 to be likely to sufficiently respond to a chemotherapy using the antitumor agent.

Item 11.

An antitumor agent comprising a PI3K/AKT/mTOR inhibitor for use in the treatment of a cancer patient who is predicted by the method according to any one of Items 1 to 6 to be likely to sufficiently respond to a chemotherapy using the antitumor agent.

The present invention further encompasses the following subject matter.

Item 12.

A method for testing therapeutic efficacy of a chemotherapy using an antitumor agent comprising a PI3K/AKT/mTOR inhibitor on a cancer patient on the basis of an expression level of PHLDA1 and/or PIK3C2B in tumor cells of the cancer patient.

Item 13.

The method according to Item 12, the method comprising the following steps (1) and (2):

(1) measuring an expression level of PHLDA1 and/or PIK3C2B in a biological sample containing tumor cells isolated from the patient; and (2) predicting that the patient is likely to sufficiently respond to the chemotherapy using the antitumor agent comprising a PI3K/AKT/mTOR inhibitor when the expression level of PHLDA1 measured in step (1) is equal to or lower than a predetermined cutoff point, or when the expression level of PIK3C2B measured in step (1) is equal to or higher than a predetermined cutoff point.

ADVANTAGEOUS EFFECTS OF INVENTION

The present invention provides a novel method for predicting the therapeutic efficacy of PI3K/AKT/mTOR inhibitors on a cancer patient. Specifically, the method of the present invention makes it possible to predict, on the basis of the expression of PHLDA1 and/or PIK3C2B, whether a cancer patient clearly exhibits sensitivity to PI3K/AKT/mTOR inhibitors. This enables the selection of appropriate drugs and the prevention of unnecessary medication in cancer treatments, thus enabling the planning of an appropriate dosing regimen or change to an appropriate dosing regimen.

DESCRIPTION OF EMBODIMENTS

The prediction method according to the present invention is for predicting or testing the therapeutic efficacy of a chemotherapy using an antitumor agent comprising a PI3K/AKT/mTOR inhibitor on a cancer patient on the basis of the expression level of PHLDA1 and/or PIK3C2B in a biological sample containing tumor cells isolated from the cancer patient.

Specific examples of cancers targeted in the present invention include head and neck cancer, digestive organ cancer (esophageal cancer, stomach cancer, duodenal cancer, liver cancer, biliary cancer (e.g., gallbladder and bile duct cancer), pancreatic cancer, small intestinal cancer, large bowel cancer (e.g., colorectal cancer, colon cancer, and rectal cancer), lung cancer (e.g., non-small cell lung cancer and small cell lung cancer), breast cancer, ovarian cancer, uterine cancer (e.g., cervical cancer, and endometrial cancer), kidney cancer, bladder cancer, and prostate cancer. The "cancer" as used herein includes not only primary tumors, but also tumors spread to other organs (e.g., liver). The "cancer patient" as used herein includes not only patients currently with tumor cells, but also patients in whom tumor cells disappeared or became undetectable by treatments such as surgical operation and chemotherapy.

The "PI3K/AKT/mTOR inhibitor" according to the present invention is not particularly limited, as long as the inhibitor can is a drug that has an inhibitory activity against signaling hyperactivity in the PI3K/AKT/mTOR signaling pathway. Examples include inhibitors that target one, or two or more molecules selected from the group consisting of PI3K, AKT, and mTOR. The inhibitor is preferably a PI3K inhibitor, an AKT inhibitor, an mTOR inhibitor, or a PI3K-mTOR dual inhibitor. These inhibitors may additionally have inhibitory activity against target molecules other than PI3K, AKT and mTOR. The term "inhibitor" as used herein includes not only drugs for inhibiting activity of target molecules, but also drugs for inhibiting the expression of target molecules. The mode of PI3K/AKT/mTOR inhibitor is not particularly limited, and examples include low-molecular compounds, antibodies, antisense oligonucleotides, siRNA, and aptamers.

In a preferable embodiment of the present invention, specific examples of PI3K/AKT/mTOR inhibitors include imidazo-oxazine compounds represented by formula (I) and their salts. The imidazo-oxazine compounds represented by formula (I) are useful as an AKT enzyme inhibitor.

In formula (I), A, B, C, and D represent C—$R^{1a}$, C—$R^{1b}$, C—$R^{1c}$, and C—$R^{1d}$, respectively, or one or two of the thus-defined A, B, C, and D are replaced by nitrogen.

Examples of halogens represented by $R^{1a}$, $R^{1b}$, $R^{1c}$, or $R^{1d}$ include chlorine, bromine, fluorine, and iodine, and preferably chlorine, and fluorine.

The $C_{1-6}$ alkyl of "$C_{1-6}$ alkyl optionally substituted with one or more hydroxyl groups" represented by $R^{1a}$, $R^{1b}$, $R^{1c}$, or $R^{1d}$ is a linear or branched alkyl having a carbon number of 1 to 6, including methyl, ethyl, n-propyl, isopropyl, n-butyl, isobutyl, sec-butyl, tert-butyl, pentyl, and hexyl, preferably $C_{1-3}$ alkyl, and more preferably methyl. The number of hydroxyl groups (substituents) is 0 to 2, and preferably 0 or 1.

The "$C_{1-6}$ alkoxy" represented by $R^{1a}$, $R^{1b}$, $R^{1c}$, or $R^{1d}$ is a linear or branched alkoxy having a carbon number of 1 to 6, including methoxy, ethoxy, n-propoxy, isopropoxy, n-butoxy, isobutoxy, and tert-butoxy, preferably $C_{1-3}$ alkoxy, and more preferably methoxy and ethoxy.

The "carbonyl having hydroxyl, amino, optionally substituted mono- or di ($C_{1-6}$ alkyl)amino or mono- or di ($C_{1-6}$ alkoxy) amino as a substituent" represented by $R^{1a}$, $R^{1b}$, $R^{1c}$, or $R^{1d}$ is carbonyl having hydroxyl as a substituent (i.e., carboxyl group), carbonyl having amino as a substituent (i.e., carbamoyl), optionally substituted mono or di($C_{1-6}$ alkyl)aminocarbonyl, or mono or di($C_{1-6}$ alkoxy)aminocarbonyl.

The "mono or di($C_{1-6}$ alkyl)aminocarbonyl" of "optionally substituted mono or di($C_{1-6}$ alkyl)aminocarbonyl" of "carbonyl having hydroxyl, amino, optionally substituted mono- or di($C_{1-6}$ alkyl)amino or mono- or di($C_{1-6}$ alkoxy) amino as a substituent" represented by $R^{1a}$, $R^{1b}$, $R^{1c}$, or $R^{1d}$ is aminocarbonyl having one or two $C_{1-6}$ alkyl groups described above, preferably mono or di ($C_{1-3}$ alkyl)aminocarbonyl, and more preferably methylaminocarbonyl, dimethylaminocarbonyl, or ethylaminocarbonyl. The substituent is preferably hydroxyl. The number of substituents, if contained, is preferably one.

The mono or di($C_{1-6}$ alkoxy)aminocarbonyl is aminocarbonyl having one or two $C_{1-6}$ alkoxy groups described above, preferably mono or di($C_{1-3}$ alkoxy)aminocarbonyl, and more preferably ethoxyaminocarbonyl.

The "carbonyl having hydroxyl, amino, optionally substituted mono- or di($C_{1-6}$ alkyl)amino or mono- or di($C_{1-6}$ alkoxy) amino as a substituent" represented by $R^{1a}$, $R^{1b}$, $R^{1c}$, or $R^{1d}$ is particularly preferably carboxyl, carbamoyl, methylaminocarbonyl, ethylaminocarbonyl, hydroxyethyl aminocarbonyl, or ethoxyaminocarbonyl.

The "unsaturated heterocyclic group" represented by $R^{1a}$, $R^{1b}$, $R^{1c}$, or $R^{1d}$ is a monocyclic or bicyclic 5- to 10-membered unsaturated heterocyclic group having one to four heteroatoms of any of N, S, and O. Examples include imidazolyl, thienyl, furyl, pyrrolyl, oxazolyl, isooxazolyl, triazolyl, isothiazolyl, pyrazolyl, triazolyl, tetrazolyl, pyridyl, pyrazyl, pyrimidinyl, pyridazinyl, indolyl, isoindolyl, indazolyl, benzofuranyl, benzoimidazolyl, benzoxazolyl, benzothiazolyl, purinyl, quinolyl, isoquinolyl, quinazolinyl, and quinoxalyl, with pyrazolyl being preferable.

Specific examples of preferable imidazo-oxazine compounds represented by formula (I) include the following compounds (a) to (t).
(a) trans-3-amino-1-cyclopropyl-3-(4-(10-fluoro-3-phenyl-5H-benzo[e]imidazo[1,2-c][1,3]oxazin-2-yl)phenyl)cyclobutanol,
(b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol,
(c) trans-3-amino-1-cyclopropyl-3-(4-(3-phenyl-5H-benzo[e]imidazo[1,2-c][1,3]oxazin-2-yl)phenyl)cyclobutanol,
(d) trans-3-amino-1-cyclopropyl-3-(4-(10-methoxy-3-phenyl-5H-benzo[e]imidazo[1,2-c][1,3]oxazin-2-yl)phenyl)cyclobutanol,
(e) trans-3-amino-1-cyclopropyl-3-(4-(9-methoxy-3-phenyl-5H-benzo[e]imidazo[1,2-c][1,3]oxazin-2-yl)phenyl)cyclobutanol,
(f) trans-3-amino-1-cyclopropyl-3-(4-(8-methoxy-3-phenyl-5H-benzo[e]imidazo[1,2-c][1,3]oxazin-2-yl)phenyl)cyclobutanol,
(g) trans-3-amino-1-cyclopropyl-3-(4-(3-phenyl-5H-imidazo[1,2-c]pyrido[2,3-e][1,3]oxazin-2-yl)phenyl)cyclobutanol,
(h) trans-3-amino-1-methyl-3-(4-(3-phenyl-5H-imidazo[1,2-c]pyrido[2,3-e][1,3]oxazin-2-yl)phenyl)cyclobutanol,
(i) trans-3-amino-1-ethyl-3-(4-(3-phenyl-5H-imidazo[1,2-c]pyrido[2,3-e][1,3]oxazin-2-yl)phenyl)cyclobutanol,
(j) trans-3-amino-1-cyclopropyl-3-(4-(3-phenyl-5H-imidazo[1,2-c]pyrido[3,4-e][1,3]oxazin-2-yl)phenyl)cyclobutanol,
(k) trans-3-amino-1-methyl-3-(4-(3-phenyl-5H-imidazo[1,2-c]pyrido[3,4-e][1,3]oxazin-2-yl)phenyl)cyclobutanol (hereinafter referred to as "Compound I"),
(l) trans-3-amino-1-cyclopropyl-3-(4-(3-phenyl-5H-imidazo[1,2-c]pyrido[4,3-e][1,3]oxazin-2-yl)phenyl)cyclobutanol,
(m) trans-3-amino-1-methyl-3-(4-(3-phenyl-5H-imidazo[1,2-c]pyrido[4,3-e][1,3]oxazin-2-yl)phenyl)cyclobutanol,
(n) trans-3-amino-1-cyclopropyl-3-(4-(3-phenyl-5H-imidazo[1,2-c]pyrido[3,2-e][1,3]oxazin-2-yl)phenyl)cyclobutanol,
(o) trans-3-amino-1-cyclopropyl-3-(4-(3-phenyl-5H-imidazo[1,2-c]pyrazino[2,3-e][1,3]oxazin-2-yl)phenyl)cyclobutanol,
(p) trans-3-amino-3-(4-(9-(hydroxy methyl)-3-phenyl-5H-benzo[e]imidazo[1,2-c][1,3]oxazin-2-yl)phenyl)-1-methylcyclobutanol,
(q) 2-(4-(trans-1-amino-3-hydroxy-3-methylcyclobutyl)phenyl)-3-phenyl-5H-benzo[e]imidazo[1,2-c][1,3]oxazine-9-carbonitrile,
(r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol,
(s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and
(t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide Examples of pharmaceutically acceptable salts of the imidazo-oxazine compounds represented by formula (I) include acid addition salts formed with inorganic acids such as hydrochloric acid, hydrobromic acid, hydroiodic acid, sulfuric acid, nitric acid, and phosphoric acid; acid addition salts formed with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluene sulfonic acid, and glutamic acid; salts formed with inorganic bases such as sodium, potassium, magnesium, calcium, and aluminium; salts formed with organic bases such as methylamine, ethylamine, meglumine, and ethanol amine; salts formed with basic amino acids such as lysine, arginine, and ornithine; and ammonium salts thereof. The imidazo-oxazine compounds represented by formula (I) include enantiomers and hydrates.

The imidazo-oxazine compounds represented by formula (I) or their pharmaceutically acceptable salts can be produced in accordance with the procedure described in WO2012/137870.

In another preferable embodiment of the present invention, specific examples of PI3K/AKT/mTOR inhibitors are as follows: specific examples of PI3K inhibitors include AMG-319, AZD-6482, BYL-719, copanlisib (BAY-80-6946), GDC-0032, GDC-0084, GSK-1059615, GSK-2126458, GSK-2636771, idelalisib (CAL-101), IPI-145, MLN-1117 (INK-1117), PA-799 (CH-5132799), pictilisib (GDC-0941), pilaralisib (XL-147), SF-1126, sonolisib (PX-866), and voxtalisib (SAR-245409, XL-765); specific examples of AKT inhibitors include afuresertib hydrochloride (GSK-2110183), ARQ-092, AZD5363, enzastaurin hydrochloride, GDC-0068, GSK-2141795, GSK690693, LY-2780301, MK-2206, perifosine, and triciribine phosphate (VQD-002); specific examples of mTOR inhibitors include AZD-2014, AZD-8055, CC-115, CC-223, DS-3078, everolimus, temsirolimus, ME-344, MLN-0128 (INK-128), OSI-027, PWT-33597, ridaforolimus, and sirolimus; and specific examples of PI3K-mTOR dual inhibitors include dactolisib (BEZ235), DS-7423, GDC-0980, NVP-BGT-226, PF-04691502, PF-05212384 (PKI-587), and PWT-33597. These inhibitors are commercially available, and can also be produced in accordance with a typically known procedure.

Of the above-listed PI3K/AKT/mTOR inhibitors, MK-2206, BEZ235, GDC-0941, sirolimus, and trans-3-amino-1-methyl-3-(4-(3-phenyl-5H-imidazo[1,2-c]pyrido[3,4-e][1,3]oxazin-2-yl)phenyl)cyclobutanol are more preferable, and trans-3-amino-1-methyl-3-(4-(3-phenyl-5H-imidazo[1,2-c]pyrido[3,4-e][1,3]oxazin-2-yl)phenyl)cyclobutanol is particularly preferable from the standpoint of stratification effects by PHLDA1 and/or PIK3C2B.

The dosage form of the antitumor agent comprising a PI3K/AKT/mTOR inhibitor according to the present invention is not particularly limited, and can suitably be selected from typically known dosage forms depending on the type of PI3K/AKT/mTOR inhibitor. Specific examples include oral drugs (e.g., tablets, coated tablets, powdered medicine, granular medicine, capsules, and liquid medicine), injectable drugs, suppositories, patches, and ointments. The antitumor agent can be prepared in accordance with a typically known procedure using a pharmacologically acceptable carrier depending on the dosage form. Examples of carriers include those that are widely used in typical drugs, such as excipients, binders, disintegrators, lubricants, diluents, solubilizing agents, suspending agents, tonicity agents, pH adjusters, buffers, stabilizers, colorants, flavoring agents, and odor-masking agents.

The "chemotherapy using an antitumor agent comprising a PI3K/AKT/mTOR inhibitor" of the present invention refers to a chemotherapy in which at least an antitumor agent comprising a PI3K/AKT/mTOR inhibitor according to the present invention is administered. The chemotherapy includes not only chemotherapy singly using the antitumor agent comprising a PI3K/AKT/mTOR inhibitor, but also chemotherapy using the antitumor agent comprising a PI3K/AKT/mTOR inhibitor in combination with one or more other antitumor agents.

The amount of the PI3K/AKT/mTOR inhibitor contained in the antitumor agent varies depending on the symptoms of the patient to be treated with the agent, the dosage form of the agent, or the like. However, the preferable amount of the PI3K/AKT/mTOR inhibitor per unit dosage form is typically about 0.05 to 1,000 mg for an oral drug, about 0.01 to 500 mg for an injectable drug, and about 1 to 1,000 mg for a suppository. The daily dose of the antitumor agent in the above-described dosage forms varies depending on the symptoms, body weight, age, gender, and other factors of the patient, and thus cannot be unconditionally determined. However, the daily dose of the agent for an adult (body weight: 50 kg) may typically be about 0.05 to 5,000 mg, and preferably 0.1 to 1,000 mg, and the agent in such an amount is preferably administered in a single dose, or in two or three divided doses per day.

The dose schedule of the chemotherapy is suitably determined in accordance with the conditions such as the type of PI3K/AKT/mTOR inhibitor, the presence or absence of a coadministered drug, the treatment history, the disease stage, the presence or absence of metastasis, and the patient's age and gender.

The chemotherapy does not make any distinction regarding whether surgery to remove a tumor is performed during the chemotherapy, or before or after the chemotherapy. The chemotherapy may be any of the following: chemotherapy that does not involve tumor removal intended largely for a life-prolonging effect; preoperative adjuvant chemotherapy involving removal of a tumor that has shrank after chemotherapy intended largely for a tumor shrinkage effect; and postoperative adjuvant chemotherapy provided for preventive purposes after removal of a tumor intended largely for suppressing the relapse or metastasis.

The "therapeutic efficacy" in the present invention can be evaluated by tumor shrinkage effects, relapse- or metastasis-suppressing effects, life-prolonging effects, and other effects as described above. The phrase "the patient is likely to sufficiently respond to the chemotherapy using the antitumor agent comprising a PI3K/AKT/mTOR inhibitor" indicates that the therapeutic efficacy on a patient exhibiting a low expression level of PHLDA1 or a high expression level of PIK3C2B is markedly superior to the therapeutic efficacy on a patient exhibiting a high expression level of PHLDA1 or a low expression level of PIK3C2B, with the superiority being demonstrated by a statistically significant difference between them.

The biological sample in the present invention is not particularly limited, as long as the sample is isolated from a cancer patient and contains tumor cells. Examples include body fluids (e.g., blood, urine, and scalp hair), tissues (e.g., biopsy tissue samples, and excised organs), the extracts thereof, and the cultures thereof. The method for isolating a biological sample can be suitably selected depending on the type of biological sample.

PHLDA1 (Pleckstrin Homology-Like Domain family A member 1), an indicator of the present invention, is one type of nucleoprotein having a pleckstrin-homology domain, and is reported to be associated with anti-apoptotic action of the insulin-like growth factors. The association of PHLDA1 with the PI3K/AKT/mTOR pathway has been unknown.

PIK3C2B (phosphatidylinositol-4-phosphate 3-kinase, catalytic subunit type 2 beta), an indicator of the present invention, is included in the PI3K superfamily. However, unlike PIK3CA, whose association with the PI3K/AKT/mTOR inhibitors has been reported, PIK3C2B is a member of the PI3K class II family and has no regulatory subunit.

In the prediction method according to the present invention, there are no particular restrictions on what is measured for measuring the expression level, as long as the expression level can be quantitatively or semiquantitatively measured. Examples include mRNA expression level, the number of DNA copies, and protein expression level.

The mRNA expression level, when selected for the measurement, can be measured using a probe or primer that specifically hybridizes to the mRNA of PHLDA1 or PIK3C2B in accordance with a conventionally used technique for measuring the expression level of mRNA, such as Northern blotting, RT-PCR, real-time PCR, DNA microarray, and in situ hybridization.

The number of DNA copies, when selected for the measurement, can be measured using a probe that specifically hybridizes to the DNA of PHLDA1 or PIK3C2B in accordance with a conventionally used technique for measuring the number of DNA copies, such as in situ hybridization, array CGH, DNA microarray, and Southern blotting.

The expression level of protein, when selected for the measurement, can be measured using an antibody that specifically recognizes the protein of PHLDA1 or PIK3C2B in accordance with a conventionally used immunoassay, such as ELISA, Western blotting, and immunohistochemical staining.

The primer and probe in the present invention can be produced as a polynucleotide that specifically hybridizes to the DNA or mRNA of human PHLDA1 or human PIK3C2B on the basis of the known base sequence information of the DNA or mRNA of human PHLDA1 or human PIK3C2B (human PHLDA1 DNA: GenBankID NC_000012.11, mRNA: GenBankID NM_007350; human PIK3C2B DNA: GenBankID NC_000001.10, mRNA: GenBankID NM_002646) in accordance with a typically known technique. The length of the primer is 10 to 50 bases, preferably 15 to 50 bases, and more preferably 18 to 35 bases. The length of the probe is 15 bases to the total base length, preferably 20 bases to the total base, and more preferably 30 bases to the total base length.

The primer and probe do not necessarily have to have perfect complementarity as long as they can specifically hybridize to the DNA or mRNA of PHLDA1 or PIK3C2B. The primer and probe are each a polynucleotide that have at least 70%, preferably at least 80%, more preferably at least 90%, yet more preferably at least 95%, and particularly more preferably at least 98% identity to the corresponding base sequence.

The phrase "specifically hybridizes" in the present invention means that under stringent hybridization conditions, a specific hybrid is formed and a non-specific hybrid is not formed. The stringent hybridization conditions can be determined on the basis of the melting temperature (Tm) of the nucleic acid that forms a hybrid in accordance with a typically known procedure. Specific examples of washing conditions that can maintain the hybridized state typically include the conditions substantially of "1×SSC, 0.1% SDS, 37° C.," more strictly the conditions substantially of "0.5× SSC, 0.1% SDS, 42° C.," and yet more strictly the conditions substantially of "0.1×SSC, 0.1% SDS, 65° C."

The probe or primer may be labeled with a typically used radioactive substance, fluorescence substance, chemiluminescent substance, or enzyme for easy detection.

The antibody in the present invention is not particularly limited, as long as the antibody can specifically recognize the protein of PHLDA1 or PIK3C2B. The antibody may be either a monoclonal antibody or a polyclonal antibody, and may be an antibody fragment such as Fab fragment and F(ab')$_2$ fragment. The antibody can be produced in accordance with a typically known procedure (e.g., Current Protocols in Molecular Biology edit. Ausubel et al. (1987), Publish. John Wiley and Sons. Section 11.12-11.13) on the basis of the known amino acid sequence information of the protein of human PHLDA1 or human PIK3C2B (human PHLDA1 GenBankID NP 031376; human PIK3C2B GenBankID NP_002637). Alternatively, commercially available antibodies can also be used. Examples of anti-human PHLDA1 antibodies for use include Abcam Cat. #ab67849 and Abnova Cat. #H00022822-B01P, and examples of anti-human PIK3C2B antibodies include Abcam Cat. #ab55589 and Abgent Cat. #AP3309a.

In the prediction method of the present invention, when a low expression level of PHLDA1 and/or a high expression level of PIK3C2B is observed in tumor cells of a cancer patient, the cancer patient is predicted to be likely to sufficiently respond to a chemotherapy using an antitumor agent comprising a PI3K/AKT/mTOR inhibitor.

The "low expression level of PHLDA1" as used herein indicates that the expression level of PHLDA1 in a patient is relatively lower among those of all cancer patients; more specifically, the expression level of PHLDA1 is equal to or lower than a predetermined cutoff point.

The cutoff point as used herein varies depending on various conditions, such as the type of the object to be measured and the type of measurement method. Thus, the present invention encompasses a broad range of inventions using a cutoff point that can vary depending on these conditions, and the cutoff point is not limited to a particular value. A specific cutoff point can be determined in accordance with various statistical analysis techniques using premeasured expression levels of PHLDA1 of cancer patients. Examples of cutoff points include the mean or median value of the expression levels of PHLDA1 of cancer patients; and a cutoff point that divides patients into low and high PHLDA1 expression groups and that is a value at which the p-value of the log-rank test conducted for the therapeutic efficacy (e.g., survival period) of the low and high PHLDA1 expression groups is minimal or less than a certain level (e.g., a value at which the p-value is less than 0.1, or a value at which the p-value is less than 0.05). Of these, the mean or median value of the PHLDA1 expression levels of cancer patients is preferable, and the mean value of the PHLDA1 expression levels of cancer patients is more preferable.

The phrase "high expression level of PIK3C2B" indicates that the expression level of PIK3C2B in a patient is relatively higher among those of all cancer patients; more specifically, the expression level of PIK3C2B is equal to or higher than a predetermined cutoff point. The cutoff point can be determined in the same manner as in the expression level of PHLDA1 described above. The mean or median value of the PIK3C2B expression levels of cancer patients is preferable, and the mean value of the PIK3C2B expression levels of cancer patients is more preferable.

The present invention also provides an antitumor agent comprising a PI3K/AKT/mTOR inhibitor for treating a cancer patient who is predicted or determined to be likely to sufficiently respond to a chemotherapy using the antitumor agent comprising a PI3K/AKT/mTOR inhibitor by the prediction method according to the present invention.

The present invention also provides the use of such an antitumor agent of the invention.

The antitumor agent according to the present invention may also be accompanied by an instruction manual, procedure manual, or the like describing the procedure to practice the prediction method according to the present invention.

The present invention also provides a kit for predicting or testing the therapeutic efficacy of a chemotherapy using the antitumor agent according to the present invention in a cancer patient. The kit according to the present invention is suitably used in order to predict or test, by the prediction method according to the present invention, the therapeutic efficacy of a chemotherapy.

For measuring the expression level of PHLDA1 and/or PIK3C2B by quantifying DNA or mRNA in a biological sample containing tumor cells isolated from a cancer patient, the kit of the present invention may comprise a primer and/or probe that is a polynucleotide that specifically hybridizes to DNA or mRNA of the human PHLDA1 or human PIK3C2B.

For measuring the expression level of PHLDA1 and/or PIK3C2B by quantifying protein (enzyme) in a biological sample containing tumor cells isolated from a cancer patient, the kit of the present invention may comprise an antibody (primary antibody) against PHLDA1 and/or PIK3C2B (enzyme) and the secondary antibody against the primary antibody, with the secondary antibody being preferably labeled with a luciferase label, radioactive label, fluorescence label, or enzyme label.

The kit of the present invention may further comprise an instruction manual or a procedure manual describing the procedure to practice the prediction method according to the present invention.

EXAMPLES

The following Examples describe the present invention in more detail. However, the present invention is, needless to say, not limited to these Examples.

Example 1

Correlation Between Expression Level of PHLDA1 or PIK3C2B and Sensitivity to PI3K/AKT/mTOR Inhibitor A cytotoxicity assay was conducted as described below using 37 cell lines from human breast cancer (AU565, BT20, BT474, BT549, CAMA-1, DU4475, HCC1187, HCC1419, HCC1428, HCC1500, HCC1569, HCC1599, HCC1806, HCC1937, HCC1954, HCC202, HCC2218, HCC38, HCC70, MDA-MB-157, MDA-MB-175, MDA-MB-231, MDA-MB-361, MDA-MB-415, MDA-MB-436, MDA-MB-453, MDA-MB-468, UACC-812, and UACC-893 (all obtained from American Type Culture Collection (ATCC); MCF-7, SK-BR-3, T47D, and ZR-75-1 (all obtained from Sumitomo Dainippon Pharma Co., Ltd.); KPL-1, KPL-3C, and KPL-4 (provided by Dr. Kurebayashi at Kawasaki Medical School)). Each cell line was seeded into a 96-well flat-bottom microplate in an amount of 150 µL, and cultured in an incubator containing 5% carbon dioxide gas at 37° C. for one day. PI3K/AKT/mTOR inhibitors (AKT inhibitor: Compound-I, MK-2206, PI3K-mTOR dual inhibitor: BEZ235, PI3K inhibitor: GDC-0941, mTOR inhibitor: sirolimus) diluted stepwise with dimethylsulfoxide, paclitaxel diluted stepwise with dimethylsulfoxide, and dimethylsulfoxide were individually added to respective media for the cell lines. 50 µL of each of the media was added to the wells of the aforementioned 96-well flat-bottom microplate so that the final concentration of each drug became 10,000, 3,000, 1,000, 300, 100, 30, 3, and 1 nM. A separately prepared 96-well flat-bottom microplate in which each cell line was cultured for one day was allowed to stand at room temperature for 30 minutes, and 50 µL of the supernatant was removed from each well to leave 100 µL of the cell culture solution. To each well containing the remaining 100 µL of the cell culture solution, the same amount of CellTiter-Glo Luminescent Cell Viability Assay (Promega, Cat. #G7573) was added. The microplate was allowed to stand in a dark place for 10 minutes, and then the luminescence intensity of live cells of each well to which the drug were added was measured using a microplate reader (PerkinElmer, ARVOsx). The cell lines to which a drug or only dimethylsulfoxide was added were further cultured at 37° C. in an incubator containing 5% carbon dioxide gas for 3 days. After culture, the cell lines were allowed to stand at room temperature for 30 minutes, and 100 µL of the supernatant was removed from each well to leave 100 µL of the cell culture solution. To the remaining 100 µL cell culture solution, the same amount of CellTiter-Glo Luminescent Cell Viability Assay was added. The microplate was allowed to stand in a dark place for 10 minutes, and then the luminescence intensity of live cells of each well was measured using a microplate reader. The cell growth rate of the 37 cell lines from human breast cancer was determined in accordance with the following equations, and the concentration at which the cell growth rate is 50%, i.e., the concentration ($GI_{50}$; (µM)) of each drug at which the cell growth is suppressed by 50%, was determined.

When $T \geq C_0$, Cell Growth Rate (%)=$(T-C_0)/(C-C_0) \times 100$
When $T \geq C_0$, Cell Growth Rate (%)=$(T-C_0)/C_0 \times 100$ $C_0$: The luminescence intensity in a well containing media with cells before a drug is added (count per second)

C: The luminescence intensity in a well containing media with cells to which only dimethylsulfoxide was added (count per second)

T: The luminescence intensity in a well containing media with cells to which a drug to be tested was added (count per second)

Subsequently, the expression level of PHLDA1 and PIK3C2B in the 37 cell lines from human breast cancer was measured. Each cell line was cultured in a 10 cm cell culture dish until about 50 to 80% confluency was achieved, and the total RNA was extracted using an RNeasy Mini Kit (Qiagen, Cat. #74106) in accordance with the instruction manual. The concentration and purity of the extracted total RNA were examined using a spectrophotometer (NanoDrop 1000, Thermo Fisher Scientific). The degradation was also examined using an Agilent 2100 Bioanalyzer (Agilent Technologies). The extracted total RNA was reverse-transcribed into cDNA using a GeneChip 3' IVT Express Kit (Affymetrix), and then further transcribed into biotinylated cRNA. Subsequently, the amplified biotinylated cRNA (20 µg) was fragmented. Each operation was conducted in accordance with the procedure of the instruction manual included with the kit. The obtained biotinylated cRNA from each cell line as a specimen was added to a GeneChip Human Genome U-133 Plus 2.0 Array (Affymetrix, PIK3C2B probe set ID:204484 at, PHLDA1 probe set ID:217997 at), and then placed in a GeneChip Hybridization Oven 640 (Affymetrix), followed by hybridization at 45° C. at 60 rpm for 16 hours. After the hybridization, each specimen was washed and fluorescence-labeled using a GeneChip Fluidics Station 450 (Affymetrix), and then scanned using a GeneChip Scanner 3000 7G (Affymetrix) to obtain microarray data. The analysis of the microarray data was performed using MATLAB (MathWorks). The gene expression level was determined by the RMA (Robust Multi-array Average) technique.

Figure 1:
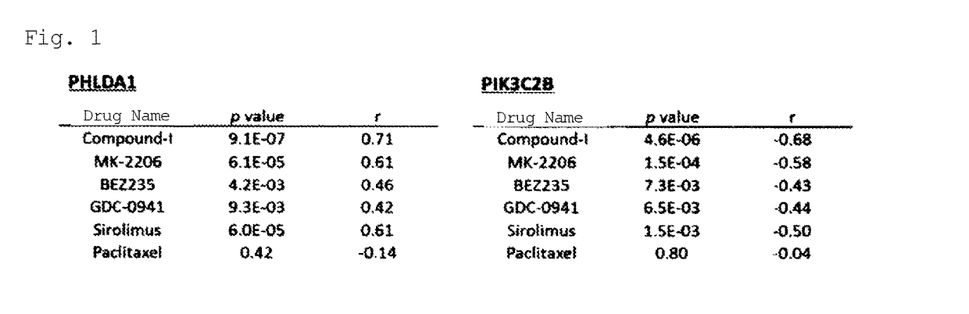
FIG. 1 shows a correlation between the expression level of PHLDA1 or PIK3C2B and the sensitivity to PI3K/AKT/mTOR inhibitors.

FIG. 1 shows the Pearson correlation between the logarithm of the above-obtained $GI_{50}$ of each drug, and the logarithm of the expression level of PHLDA1 and PIK3C2B.

The results reveal that all of the examined PI3K/AKT/mTOR inhibitors had a statistically significant positive correlation with the expression level of PHLDA1, and also had a statistically significant negative correlation with the expression level of PIK3C2B. Paclitaxel, however, did not show a correlation with the expression level of either PHLDA1 or PIK3C2B. Specifically, the results indicate that the expression level of PIK3C2B and PHLDA1 can be a sensitivity predictive marker for a wide range of PI3K/AKT/mTOR inhibitors.

It was also examined whether the expression level of PHLDA1 or PIK3C2B has a correlation with the sensitivity to PI3K/AKT/mTOR inhibitors in a panel of 240 cell lines (OncoPanel™, Ricerca Biosciences) composed of various cancers such as lung cancer, kidney cancer, liver cancer, pancreatic cancer, large bowel cancer, bladder cancer, breast cancer, head and neck cancer, prostate cancer, skin cancer, blood cancer, and malignant lymphoma. The results revealed that, as in the 37 cell lines from human breast cancer, there was a significant correlation between the logarithm of the GI$_{50}$ of a wide range of PI3K/AKT/mTOR inhibitors (Compound-I, MK-2206, BEZ235, GDC-0941, and sirolimus) and the logarithm of the expression level of PHLDA1 and PIK3C2B in the panel of 240 cell lines.

Example 2

Analysis of PHLDA1 Gene Knockdown, Expression Level of Protein, and Phosphorylated State PHLDA1 gene was knocked down to examine the phosphorylated state of AKT, and the relation between PHLDA1 and the PI3K/AKT/mTOR signaling pathway was analyzed.

Three breast cancer cell lines (HCC38, HCC1806, HCC1937; all were obtained from American Type Culture Collection (ATCC)), which showed a relatively high expression of PHLDA1, were cultured in an RPMI medium (Life Technologies Corp., Cat. #A104910-01) containing 10% FBS.

Negative control siRNA (ON-TARGET Plus control pool, Thermo Fisher Scientific, Cat. #D-001810-10-20) and PHLDA1-siRNA (ON-TARGET Plus siRNA Human PHLDA1, Thermo Fisher Scientific, Cat. #J-012389-08) were prepared for the cell lines at a final concentration of 10 nM. The siRNA was introduced into the cells using Lipofectamine RNAiMAX (Life Technologies, Cat. #13778-150) in accordance with the instruction manual to knockdown the gene. After 3-day knockdown, the cell lines were washed with cool PBS (Life Technologies, Cat. #10010-023) twice, and a solubilized buffer (PhosSTOP (Roche, Cat. #4906837), complete, and a Pierce RIPA Buffer (Thermo Fisher Scientific, Cat. #89901)) containing EDTA-free (Roche, Cat. #1873580) were added to the washed cell lines, followed by cooling with ice for 30 minutes for solubilization. The solubilized extracts were centrifuged at 4° C. and 15,000 rpm for 30 minutes to collect the supernatants, thereby giving protein extracts. The obtained protein extracts were measured for protein concentration using a BCA Protein Assay Reagent (Thermo Fisher Scientific, Cat. #23225) in accordance with the instruction manual. A reducing buffer (ImmunoPure Lane Marker Reducing Sample Buffer (Thermo Fisher Scientific, Cat. #39000)) was added to the protein extracts, and the extracts were boiled and thereby modified. 20 μg of each reduced protein extract was applied to Criterion TGX Precast Gels (Bio-Rad, Cat. #567-1084) per lane, and SDS-PAGE was conducted.

Figure 2:
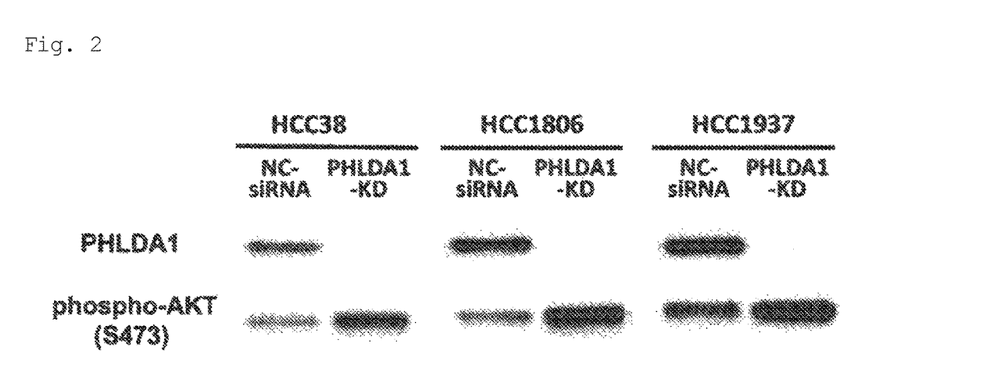
FIG. 2 shows the analysis results of PHLDA1 gene knockdown, the expression level of protein, and the phosphorylated state.

After completion of SDS-PAGE, the proteins were transferred to respective PVDF membranes (Trans-Blot Turbo Midi PVDF Transfer Pack, Bio-Rad, Cat. #170-4157) using a blotting apparatus (Trans-Blot Turbo Transfer System, Bio-Rad). The transferred membranes were incubated at room temperature for 1 hour to perform blocking with Blocking One-P (Nacalai, Cat. #05999-84). Subsequently, the membranes were reacted, at 4° C. overnight, with an anti-human PHLDA1 goat antibody (Santa Cruz, Cat. #sc-6142) and an anti-human phosphorylated AKT rabbit antibody (S473) (Cell Signaling Technology, Cat. #4060) that had been diluted beforehand 1,000 times and 2,000 times, respectively, with a TBS buffer ("TBS-T") containing 5% BSA and 0.05% Tween20. The PVDF membranes were washed with TBS-T three times at room temperature for 10 minutes, and then reacted at room temperature for 1 hour with secondary antibodies (an anti-goat antibody (Santa Cruz, Cat. #sc-2020) and an anti-rabbit antibody (GE Healthcare, Cat. #NA9340V) that had been labeled with horseradish peroxidase (HRP)) diluted 2,000 times with 5% skim milk/TBS-T. The PVDF membranes were washed with TBS-T three times at room temperature for 10 minutes, and then the chemiluminescence was detected with LAS-3000 (Fujifilm) using an ECL Prime Western Blotting Detection Reagent (GE Healthcare, Cat. #RPN2232). FIG. 2 shows the results.

As shown in FIG. 2, in the three breast cancer cell lines that exhibit a high expression of PHLDA1, the PHLDA1 gene knockdown led to an increase in AKT phosphorylation (S473) as well as activation of the PI3K/AKT/mTOR signaling pathway. Because the AKT phosphorylation (S473) level correlates with in vitro and in vivo antitumor effects of PI3K inhibitors (Cancer Research 70, 4982-4994 (2010)), the results indicate that the expression level of PHLDA1 can be associated with the therapeutic efficacy of PI3K/AKT/mTOR inhibitors.

Example 3

Analysis of Change in Sensitivity to PI3K/AKT/mTOR Inhibitor Caused by PIK3C2B Gene Knockdown A human ovarian cancer cell line OVCAR-3 (obtained from ATCC) was cultured in an RPMI medium (Life Technologies Corp., Cat. #A104910-01) containing 20% FBS and 0.01 mg/mL bovine insulin (Sigma-Aldrich, Cat. #I0516). A human breast cancer cell line HCC1187 (obtained from ATCC) was cultured in an RPMI medium (Life Technologies Corp., Cat. #A104910-01) containing 10% FBS.

Figure 3:
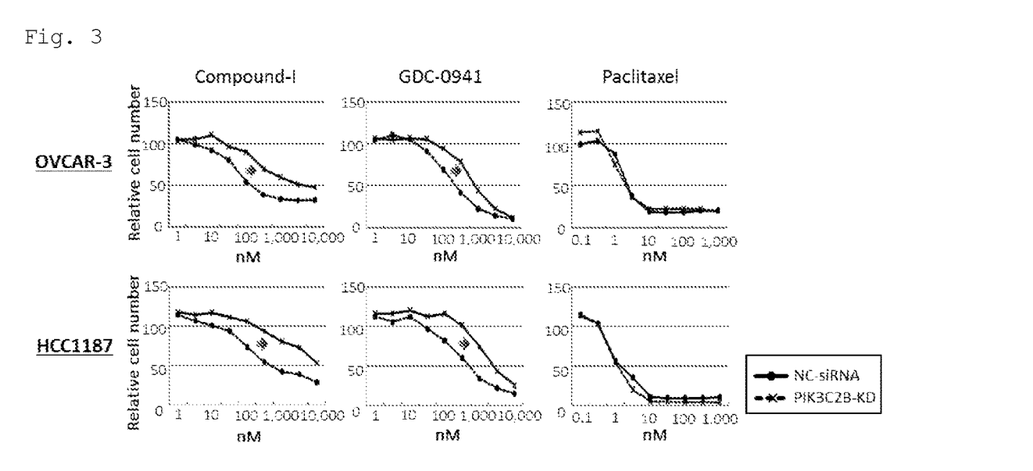
FIG. 3 shows the analysis results of change in the sensitivity to PI3K/AKT/mTOR inhibitors caused by PIK3C2B gene knockdown.

Cytotoxicity of PI3K/AKT/mTOR inhibitors (AKT inhibitor: Compound-I, PI3K inhibitor: GDC-0941) and paclitaxel to the cell lines was assayed in accordance with Example 1. FIG. 3 shows the relative cell count of the cell lines treated with drugs of different concentrations, assuming that the cell count of control cells (dimethylsulfoxide added) cultured for three days is 100, and the absence of cell is 0.

As shown in FIG. 3, in OVCAR-3 and HCC1187 cell lines, the PIK3C2B gene knockdown led to a decrease in sensitivity to Compound-I and GDC-0941, which are PI3K/AKT/mTOR inhibitors. However, almost no change was observed in sensitivity to paclitaxel, which is not a PI3K/AKT/mTOR inhibitor. Specifically, the results reveal that PIK3C2B is a determining factor that can alone regulate the sensitivity of cancer cells to a PI3K/AKT/mTOR inhibitor.

Example 4

Comparison of PHLDA1/PIK3C2B Expression Level Measurement with Conventional PIK3CA Mutation/PTEN Deletion Measurement in PI3K/AKT/mTOR Inhibitor Therapeutic Efficacy Predicting Performance The expression level of PHLDA1 or PIK3C2B was compared with PIK3CA mutation or PTEN deletion, which have been examined as a therapeutic efficacy predictive marker in clinical practice, in terms of the correlation with the sensitivity to a PI3K/AKT/mTOR inhibitor.

Figure 4:
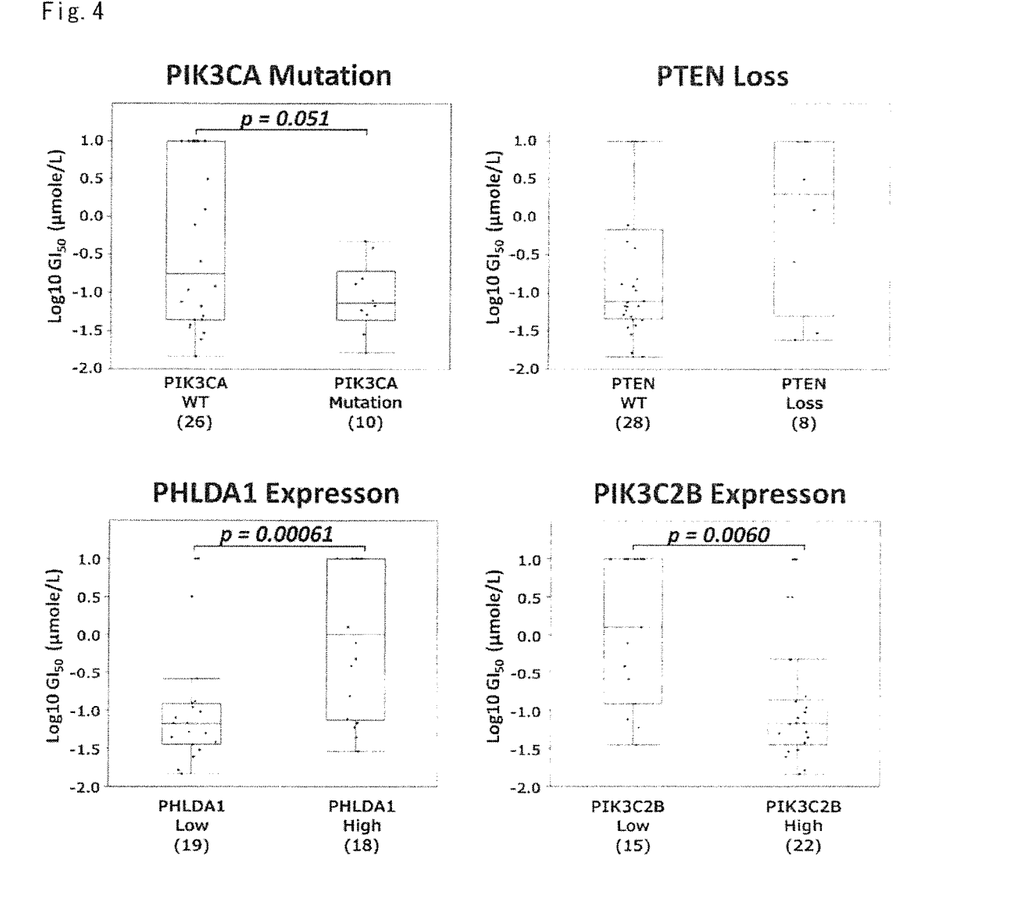
FIG. 4 shows a comparison of the PHLDA1/PIK3C2B expression level measurement with the conventional PIK3CA mutation/PTEN deletion measurement in PI3K/AKT/mTOR inhibitor therapeutic efficacy predicting performance.

Of the 37 cell lines from human breast cancer described in Example 1, 36 cell lines (KPL-3C is excluded) have been known to have PIK3CA mutation or PTEN deletion. FIG. 4 shows the GI$_{50}$ (μM) of Compound-I for the 36 cell lines with the presence or absence of PIK3CA mutation (E545K or H1047R) or PTEN deletion. PTEN deletion (8 cell lines) did not show a correlation with the sensitivity to Compound-I. PIK3CA mutation (10 cell lines) demonstrated a tendency to correlate with a high sensitivity to Compound-I, but the correlation was not significant (P=0.051). Likewise, studies were conducted on the association of the expression level of PHLDA1 or PIK3C2B with the sensitivity to Compound-I in the 37 cell lines from human breast cancer. FIG. 4 shows, as an example, the distribution of $GI_{50}$ (μM) of Compound-I in the case where the mean value of the expression levels of PHLDA1 or PIK3C2B was determined as a cutoff point, and the expression levels were divided into two groups. The expression level of each PHLDA1 and PIK3C2B showed a strong correlation with the sensitivity to Compound-I (P=0.00061, and 0.0060).

The expression level of PHLDA1 or PIK3C2B clearly has a higher correlation with the sensitivity to Compound-I than the conventional techniques, PIK3CA mutation and PTEN deletion, and is useful as a therapeutic efficacy predictive marker in clinical practice.

The invention claimed is:

1. A method for identifying a cancer patient as likely to sufficiently respond to chemotherapy using an antitumor agent comprising a PI3K/AKT/mTOR inhibitor and for treating said patient, comprising
   a) measuring an expression level of PHLDA1 and/or PIK3C2B in a biological sample containing tumor cells isolated from the cancer patient, wherein the cancer patient is suffering a cancer selected from the group consisting of breast cancer, ovarian cancer and uterine cancer; and
   b) identifying a cancer patient as likely to sufficiently respond to chemotherapy using the antitumor agent comprising a PI3K/AKT/mTOR inhibitor when the expression level of PHLDA1 measured in step a) is equal to or lower than a predetermined cutoff point, or when the expression level of PIK3C2B measured in step a) is equal to or higher than a predetermined cutoff point,
   wherein the predetermined cutoff point for the expression level of PHLDA1 is the mean or median value of the PHLDA1 expression levels of cancer patients or a value at which the p-value of the log-rank test conducted for the therapeutic efficacy is less than 0.1 and wherein the predetermined cutoff point for the expression level of PIK3C2B is the mean or median value of the PIK3C2B expression levels of cancer patients or a value at which the p-value of the log-rank test conducted for the therapeutic efficacy is less than 0.1; and
   c) administering the antitumor agent comprising a PI3K/AKT/mTOR inhibitor, to said cancer patient, wherein the PI3K/AKT/mTOR inhibitor is an imidazo-oxazine compound represented by formula (I) or its pharmaceutically acceptable salt (I)

wherein
A, B, C, and D represent C—$R^{1a}$, C—$R^{1b}$, C—$R^{1c}$, and C—$R^{1d}$, respectively, or one or two of the thus-defined A, B, C, and D are replaced by nitrogen;

at least two of $R^{1a}$, $R^{1b}$, $R^{1c}$, and $R^{1d}$ represent hydrogen, and the other(s) each represent(s) halogen, cyano, $C_{1-6}$ alkyl optionally substituted with one or more hydroxyl groups, $C_{1-6}$ alkoxy, carbonyl having hydroxyl, amino, optionally substituted mono- or di($C_{1-6}$ alkyl)amino or mono- or di($C_{1-6}$ alkoxy)amino as a substituent, or unsaturated heterocyclic group;
$R^2$ represents phenyl, pyridyl, or thienyl;
$R^3$ represents hydrogen, methyl, ethyl, or cyclopropyl; and
$R^4$ represents hydrogen or hydroxyl.

2. The method according to claim 1, further comprising obtaining a biological sample containing tumor cells from a cancer patient before step a).

3. The method according to claim 1, wherein the imidazo-oxazine compound represented by formula (I) is a compound wherein A, B, C, and D represent C—$R^{1a}$, C—$R^{1b}$, C—$R^{1c}$, and C—$R^{1d}$, respectively, or any one or two of the thus-defined A, B, C, and D are replaced by nitrogen;
at least two of $R^{1a}$, $R^{1b}$, $R^{1c}$, and $R^{1d}$ represent hydrogen, and the other(s) each represent(s) chlorine, fluorine, cyano, methyl, hydroxymethyl, methoxy, ethoxy, carboxyl, carbamoyl, methylaminocarbonyl, ethylaminocarbonyl, hydroxyethylaminocarbonyl, ethoxyaminocarbonyl, or pyrazolyl;
$R^2$ represents phenyl, pyridyl, or thienyl;
$R^3$ represents hydrogen, methyl, ethyl, or cyclopropyl; and
$R^4$ represents hydrogen or hydroxyl.

4. The method according to claim 1, wherein the imidazo-oxazine compound represented by formula (I) is any of the following compounds (a) to (t),
(a) trans-3-amino-1-cyclopropyl-3-(4-(10-fluoro-3-phenyl-5H-benzo[e]imidazo[1,2-c][1,3]oxazin-2-yl)phenyl)cyclobutanol,
(b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol,
(c) trans-3-amino-1-cyclopropyl-3-(4-(3-phenyl-5H-benzo[e]imidazo[1,2-c][1,3]oxazin-2-yl)phenyl)cyclobutanol,
(d) trans-3-amino-1-cyclopropyl-3-(4-(10-methoxy-3-phenyl-5H-benzo[e]imidazo[1,2-c][1,3]oxazin-2-yl)phenyl)cyclobutanol,
(e) trans-3-amino-1-cyclopropyl-3-(4-(9-methoxy-3-phenyl-5H-benzo[e]imidazo[1,2-c][1,3]oxazin-2-yl)phenyl)cyclobutanol,
(f) trans-3-amino-1-cyclopropyl-3-(4-(8-methoxy-3-phenyl-5H-benzo[e]imidazo[1,2-c][1,3]oxazin-2-yl)phenyl)cyclobutanol,
(g) trans-3-amino-1-cyclopropyl-3-(4-(3-phenyl-5H-imidazo[1,2-c]pyrido[2,3-e][1,3]oxazin-2-yl)phenyl)cyclobutanol,
(h) trans-3-amino-1-methyl-3-(4-(3-phenyl-5H-imidazo[1,2-c]pyrido[2,3-e][1,3]oxazin-2-yl)phenyl)cyclobutanol,
(i) trans-3-amino-1-ethyl-3-(4-(3-phenyl-5H-imidazo[1,2-c]pyrido[2,3-e][1,3]oxazin-2-yl)phenyl)cyclobutanol,
(j) trans-3-amino-1-cyclopropyl-3-(4-(3-phenyl-5H-imidazo[1,2-c]pyrido[3,4-e][1,3]oxazin-2-yl)phenyl)cyclobutanol,
(k) trans-3-amino-1-methyl-3-(4-(3-phenyl-5H-imidazo[1,2-c]pyrido[3,4-e][1,3]oxazin-2-yl)phen yl)cyclobutanol,

(l) trans-3-amino-1-cyclopropyl-3-(4-(3-phenyl-5H-imidazo[1,2-c]pyrido[4,3-e][1,3]oxazin-2-yl)phenyl)cyclobutanol,
(m) trans-3-amino-1-methyl-3-(4-(3-phenyl-5H-imidazo[1,2-c]pyrido[4,3-e][1,3]oxazin-2-yl)phen yl)cyclobutanol,
(n) trans-3-amino-1-cyclopropyl-3-(4-(3-phenyl-5H-imidazo[1,2-c]pyrido[3,2-e][1,3]oxazin-2-yl)phenyl)cyclobutanol,
(o) trans-3-amino-1-cyclopropyl-3-(4-(3-phenyl-5H-imidazo[1,2-c]pyrazino[2,3-e][1,3]oxazin-2-yl)phenyl)cyclobutanol,
(p) trans-3-amino-3-(4-(9-(hydroxymethyl)-3-phenyl-5H-benzo[e]imidazo[1,2-c][1,3]oxazin-2-yl)phenyl)-1-methylcyclobutanol,
(q) 2-(4-(trans-1-amino-3-hydroxy-3-methylcyclobutyl)phenyl)-3-phenyl-5H-benzo[e]imidazo[1,2-c][1,3]oxazine-9-carbonitrile,
(r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol,
(s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and
(t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

5. A method for treating a cancer patient, comprising administering an antitumor agent comprising a PI3K/AKT/mTOR inhibitor to a cancer patient with an expression level of PHLDA1 equal to or lower than a predetermined cutoff point, or an expression level of PIK3C2B equal to or higher than a predetermined cutoff point, wherein the expression level of PHLDA1 and/or PIK3C2B is measured in a biological sample containing tumor cells isolated from the cancer patient, wherein the cancer patient is suffering a cancer selected from the group consisting of breast cancer, ovarian cancer and uterine cancer, wherein the predetermined cutoff point for the expression level of PHLDA1 is the mean or median value of the PHLDA1 expression levels of cancer patients or a value at which the p-value of the log-rank test conducted for the therapeutic efficacy is less than 0.1 and wherein the predetermined cutoff point for the expression level of PIK3C2B is the mean or median value of the PIK3C2B expression levels of cancer patients or a value at which the p-value of the log-rank test conducted for the therapeutic efficacy is less than 0.1; and
wherein the PI3K/AKT/mTOR inhibitor is an imidazooxazine compound represented by formula (I) or its pharmaceutically acceptable salt wherein
A, B, C, and D represent C—$R^{1a}$, C—$R^{1b}$, C—$R^{1c}$, and C—$R^{1d}$, respectively, or one or two of the thus-defined A, B, C, and D are replaced by nitrogen;
at least two of $R^{1a}$, $R^{1b}$, $R^{1c}$, and $R^{1d}$ represent hydrogen, and the other(s) each represent(s) halogen, cyano, $C_{1-6}$ alkyl optionally substituted with one or more hydroxyl groups, $C_{1-6}$ alkoxy, carbonyl having hydroxyl, amino, optionally substituted mono- or di($C_{1-6}$ alkyl)amino or mono- or di($C_{1-6}$ alkoxy)amino as a substituent, or unsaturated heterocyclic group;
$R^2$ represents phenyl, pyridyl, or thienyl;
$R^3$ represents hydrogen, methyl, ethyl, or clopropyl; and'
$R^4$ represents hydrogen or hydroxyl.

6. A method for predicting therapeutic efficacy of a chemotherapy using an antitumor agent comprising a PI3K/AKT/mTOR inhibitor, on a cancer patient, and for treating said patient, comprising
a) measuring an expression level of PHLDA1 and/or PIK3C2B in a biological sample containing tumor cells isolated from the cancer patient, wherein the cancer patient is suffering from a cancer selected from the group consisting of breast cancer, ovarian cancer and uterine cancer; and
b) identifying a cancer patient as likely to sufficiently respond to chemotherapy using the antitumor agent comprising a PI3K/AKT/mTOR inhibitor when the expression level of PHLDA1 measured in step a) is equal to or lower than a predetermined cutoff point, or when the expression level of PIK3C2B measured in step a) is equal to or higher than a predetermined cutoff point,
wherein the predetermined cutoff point for the expression level of PHLDA1 is the mean or median value of the PHLDA1 expression levels of cancer patients or a value at which the p-value of the log-rank test conducted for the therapeutic efficacy is less than 0.1 and wherein the predetermined cutoff point for the expression level of PIK3C2B is the mean or median value of the PIK3C2B expression levels of cancer patients or a value at which the p-value of the log-rank test conducted for the therapeutic efficacy is less than 0.1; and
c) performing chemotherapy by administering the antitumor agent to said cancer patient,
wherein the PI3K/AKT/mTOR inhibitor is an imidazooxazine compound represented by formula (I) or its pharmaceutically acceptable salt:

wherein
A, B, C, and D represent C—$R^{1a}$ a C—$R^{1b}$, C—$R^{1c}$ and C—$R^{1d}$, respectively, or one or two of A, B, C, and D are replaced by nitrogen;
at least two of $R^{1a}$, $R^{1b}$, $R^{1c}$ and $R^{1d}$ represent hydrogen, and the other(s) each represent(s) halogen, cyano, $C_{1-6}$ alkyl unsubstituted or substituted with one or more hydroxyl groups, $C_{1-6}$ alkoxy, carbonyl having hydroxyl, amino, unsubstituted or substituted mono- or di($C_{1-6}$ alkyl)amino or mono- or di($C_{1-6}$ alkoxy)amino as a substituent, or unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxyl.

7. A method for predicting therapeutic efficacy of chemotherapy using an antitumor agent comprising a AKT/mTOR inhibitor on a cancer patient, and for treating said patient, comprising
 a) measuring an expression level of PHLDA1 and/or PIK3C2B in a biological sample containing tumor cells isolated from the cancer patient, wherein the cancer patient is suffering from a cancer selected from the group consisting of breast cancer, ovarian cancer and uterine cancer; and
 b) identifying a patient as likely to respond to chemotherapy using the antitumor agent comprising a AKT/mTOR inhibitor when the expression level of PHLDA1 measured in step a) is equal to or lower than a predetermined cutoff point, or when the expression level of PIK3C2B measured in step a) is equal to or higher than a predetermined cutoff point, wherein the predetermined cutoff point for the expression level of PHLDA1 is the mean or median value of the PHLDA1 expression levels of cancer patients or a value at which the p-value of the log-rank test conducted for the therapeutic efficacy is less than 0.1 and wherein the predetermined cutoff point for the expression level of PIK3C2B is the mean or median value of the PIK3C2B expression levels of cancer patients or a value at which the p-value of the log-rank test conducted for the therapeutic efficacy is less than 0.1; and
 c) performing chemotherapy by administering the antitumor agent to saki cancer patient, wherein the PI3K/AKT/mTOR inhibitor is an imidazooxazine compound represented by formula (I) or its pharmaceutically acceptable salt wherein A, B, C, and D represent C—$R^{1a}$, C—$R^{1b}$, C—$R^{1c}$, and C—$R^{1d}$, respectively, or one or two of the thus-defined A, B, C, and D are replaced by nitrogen;

at least two of $R^{1a}$, $R^{1b}$, $R^{1c}$, and $R^{1d}$ represent hydrogen, and the other(s) each represent(s) halogen, cyano, $C_{1-6}$ alkyl optionally substituted with one or more hydroxyl groups, $C_{1-6}$ alkoxy, carbonyl having hydroxyl, amino, optionally substituted mono- or di($C_{1-6}$ alkyl)amino or mono- or di($C_{1-6}$ alkoxy)amino as a substituent, or unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxyl.

* * * * *

UNITED STATES PATENT AND TRADEMARK OFFICE
CERTIFICATE OF CORRECTION

PATENT NO.        : 10,155,990 B2
APPLICATION NO.   : 14/895286
DATED             : December 18, 2018
INVENTOR(S)       : Tetsuya Abe It is certified that error appears in the above-identified patent and that said Letters Patent is hereby corrected as shown below:

(72) Inventors read:
"Hiraku ITAKDANI"
Should read:
--Hiraku ITADANI--

Signed and Sealed this
Third Day of September, 2019

Andrei Iancu
*Director of the United States Patent and Trademark Office*